United States Patent [19]

Viertl et al.

[11] Patent Number: 4,593,245
[45] Date of Patent: Jun. 3, 1986

[54] EDDY CURRENT METHOD FOR DETECTING A FLAW IN SEMI-CONDUCTIVE MATERIAL

[75] Inventors: John R. M. Viertl; Mederic E. Auger, both of Schenectady, N.Y.

[73] Assignee: General Electric Company, Schenectady, N.Y.

[21] Appl. No.: 560,214

[22] Filed: Dec. 12, 1983

[51] Int. Cl.[4] .................... G01N 27/90; G01R 33/12
[52] U.S. Cl. .................................... 324/238; 324/262; 336/200
[58] Field of Search ............... 324/202, 207, 208, 225, 324/229, 230, 233, 234, 236–243, 262; 336/200, 205, 206, 232

[56] References Cited

U.S. PATENT DOCUMENTS

| | | | |
|---|---|---|---|
| 2,955,253 | 10/1960 | Bryant et al. | 324/238 |
| 3,132,299 | 5/1964 | Hochschild | 324/238 |
| 3,568,049 | 3/1971 | Barton . | |
| 3,901,368 | 8/1975 | Klinger | 324/239 X |
| 3,988,665 | 10/1976 | Neumaier et al. | 324/240 |
| 4,107,605 | 8/1978 | Hudgell . | |
| 4,109,201 | 8/1978 | Pigeon et al. | 324/238 X |
| 4,437,062 | 3/1984 | Donnelly | 324/238 |

FOREIGN PATENT DOCUMENTS

| | | | |
|---|---|---|---|
| 3137222 | 4/1983 | Fed. Rep. of Germany | 324/207 |
| 700830 | 11/1979 | U.S.S.R. | 324/238 |
| 824020 | 4/1981 | U.S.S.R. | 324/240 |

Primary Examiner—Gerard R. Strecker
Attorney, Agent, or Firm—Paul Checkovich; Jerome C. Squillaro

[57] ABSTRACT

An eddy current probe, excitable at frequencies equal to or greater 7 mhz., includes a substantially planar, spiral-like, unilaminar coil mounted on an insulative substrate. A protective layer covers the coil and is adapted to present only a minimal mechanical barrier between the coil and a region of material under test. The coil is a continuous run of copper having an effective diameter no greater than 2 mils. The coil, substrate and protective layer are a printed circuit board. A method of detecting flaws is also disclosed.

8 Claims, 7 Drawing Figures

EDDY CURRENT METHOD FOR DETECTING A FLAW IN SEMI-CONDUCTIVE MATERIAL

BACKGROUND OF THE INVENTION

This invention relates to an apparatus and method for detecting flaws in the surface and sub-surface region of a material by inducing an eddy current therein at a relatively high frequency.

The ability of an eddy current probe to detect flaws in the surface and sub-surface region of materials depends upon the resistivity of the material and the excitation frequency applied to the coil within the eddy current probe. The resistivity of a material provides a classification of the material as conducting or semi-conducting, hence, a material having a relatively high value of resistivity is commonly recognized as semi-conducting in nature. To nondestructively test a semi-conducting material, a relatively high frequency is necessary to induce an eddy current within the material. For example, to detect a hair line surface crack in a block of carbon, the eddy current probe must have its coil excited at a relatively high frequency, a frequency which approaches 6 megahertz.

The excitation frequency of the coil also affects the depth of penetration of the eddy currents in the material under test. As commonly recognized in the nondestructive testing art, the higher the frequency of excitation, the lesser the depth of penetration within the sub-surface region of the material under test. If the depth of penetration in the above example is limited to approximately 35 mils, the coil must be excited at a frequency equal to or greater than 7 megahertz.

High sensitivity, commercially available, eddy current probes have an upper frequency range limitation of 6 megahertz. An example of one high frequency eddy current probe is the SPO2000 Probe manufactured by Nortec Inc. of Kennewick, Wash. These high sensitivity probes generally have fine wire wound about a small bobbin. To achieve the high sensitivity to detect the hair line surface crack in the carbon block example, the coil therein must be excited by a signal approaching or exceeding 7 megahertz. At that high frequency, the interwire capacitance between the turns in the coil generally acts as a capacitive shunt across the entire coil. This shunt effectively shorts out the coil's output, hence the probe no longer functions properly.

The high frequency required in the above example dictates a reduction in the number of turns of the coil and an enlargement of the spacing between each turn. Other considerations require that the coil quality factor (Q) be greater than 1 and preferably be greater than 10. As is well known in the art, the coil quality factor is related to the ratio between the energy stored in the coil and the energy dissipated in the coil. The AC coil losses are functionally related to the energy dissipated and are dependent upon the diameter of the wire. For frequencies on the order of 7 megahertz, the wire diameter must be less than or equal to 2 mils. If the frequency is increased to 10 megahertz, a wire having a diameter of 1.4 mils is recommended.

The construction of a coil with wire less than or equal to 2 mils is very difficult due to the fineness and fragility of the wire. An additional factor to be considered is the geometry of the coil. In the carbon block example above, the precise location of the hair line surface crack is not known. Hence, the surface area to be covered by the coil is relatively large in relation to the depth of penetration of the eddy current in the material. As recognized in the art, the geometric configuration of the windings of the coil is important for the faithful reproduction of the coil. It is desirable to obtain at least two coils having similar levels of impedance. To meet the above requirements for the carbon block example, i.e., small depth penetration by the eddy currents, relatively large surface area, a relatively high excitation frequency, windings having a diameter on the order of 2 mils, and uniform but relatively large spacing between each winding (to minimize interwire capacitance), the coil must be substantially planar. A planar coil induces an eddy current in the carbon material over a large surface area and if the excitation frequency is high, at a relatively limited depth into the sub-surface region of the carbon block.

Experiments have shown that a fine wire, having a diameter of 2 mils, 44 gage AWG, placed on a planar insulating surface, cannot be replicated with sufficient accuracy. Thus the coils constructed by this method had impedances varying from coil to coil by approximately 10%. The variation in impedances between these experimental coils is not acceptable when the coils are utilized to detect flaws in materials. It is known that planar, unilaminar coils have been utilized as inductors on printed circuit boards. However, those printed circuit board inductors do not necessarily generate uniform electromagnetic fields proximate their coils.

OBJECTS OF THE INVENTION

It is an object of this invention to provide for an apparatus to detect flaws in the surface and sub-surface region of a semi-conducting or conducting material which possesses a high degree of sensitivity, and includes a coil excitable at a frequency equal to or greater than 7 megahertz.

It is another object of this invention to provide for an apparatus which is reproducible such that similarly constructed coils have substantially comparable impedances when those coils are excited at the same frequency.

It is a further object of this invention to provide for a coil which may be placed over a cambered support surface.

An additional object of the present invention provides for an eddy current coil mounted on an insulative substrate and both are a printed circuit board.

SUMMARY OF THE INVENTION

An apparatus, which detects flaws in the surface and sub-surface region of a semi-conducting or conducting material, includes means for generating a uniform electromagnetic field normal to a substantially planar, spiral-like, unilaminar coil mounted on an insulative substrate. A protective insulative layer covers the coil and is adapted to present only a minimal mechanical barrier between the coil and the region of material under test. In one embodiment, the coil includes a continuous run of metal, such as copper, having an effective diameter no greater than 2 mils. In a further embodiment of the present invention, the coil and substrate is a printed circuit board.

The invention additionally includes means for detecting the impedance of the coil and providing a representative signal, means for establishing a reference signal, means for placing the coil adjacent the region of material under test, and a comparison means. The comparison means provides an output signal indicative of the integrity of the region of material under test by relating the reference signal to the measured impedance signal.

In another embodiment of this invention, the unilaminar coil is substantially planar but cambered and is mounted on an insulative substrate.

A method of detecting flaws in the surface and sub-surface region of the material includes the steps of: providing a continuous run of metal on a substantially planar insulative substrate as a unilaminar coil, providing means for exciting said coil, establishing a reference signal, juxtapositioning the coil adjacent the region of material under test to induce an electromagnetic field therein, and comparing a signal representative of the impedance of the coil with the reference signal to provide an output signal indicative of the integrity of the material under test.

BRIEF DESCRIPTION OF THE DRAWINGS

The subject matter which is regarded as the invention is particularly pointed and distinctly claimed in the concluding portion of the specification. The invention, however, together with further objects and advantages thereof, may best be understood by reference to the following description taken in connection with the accompanying drawings in which:

DETAILED DESCRIPTION OF THE INVENTION

The present invention relates generally to an eddy current coil which is operated at a frequency equal to or greater than 7 megahertz thereby inducing an eddy current in a semi-conducting material at a relatively minimal depth of penetration.

Figure 1:
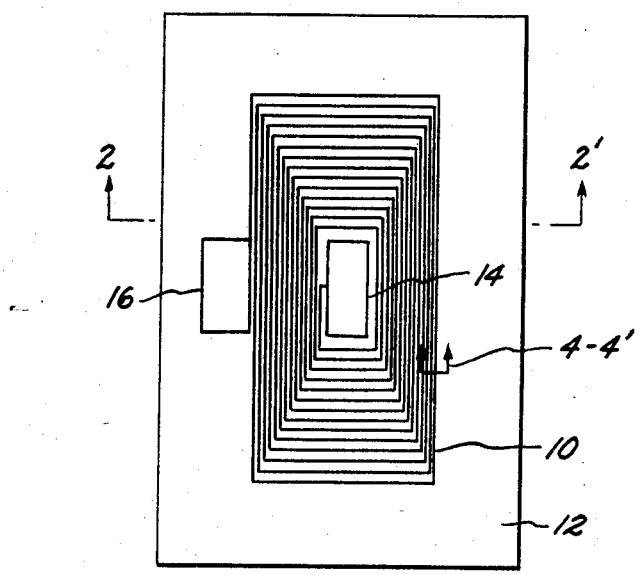
FIG. 1 illustrates a magnified, top view of an eddy current coil with which the invention may be practiced.

FIG. 1 illustrates the top view of eddy current coil 10 mounted on a substantially planar insulative substrate 12. Coil 10 and substrate 12 are part of means for generating a substantially uniform electromagnetic field extending normal to the surface of substrate 12. Coil 10 includes a continuous run of metal geometrically configured spiral-like on substrate 12. As used herein, the term "spiral-like" means a unilaminar coil having one end centrally located and the run of metal completely surrounding that centrally located end. The run of metal is wound about itself and has a second end spacially displaced from the centrally located end on the generally planar surface of the substrate. Hence, the spiral-like geometric configuration of the coil in FIG. 1 possesses squared corners, but nonetheless, coil 10 is considered spiral-like for the purposes of this invention.

Coil 10 is a 14 turn coil composed substantially of copper having an effective diameter of approximately 0.7 mils. It is to be understood that although the effective diameter of a run of copper in coil 10 is 0.7 mils, the invention could utilize a run of copper, or other metal such as silver or platinum, having an effective diameter no greater than 2 mils. Coil 10 is easily reproducible because coil 10 and substrate 12 is a printed circuit board. Solder pad 14 is electrically connected to the centrally located end of coil 10. Solder pad 16 is electrically connected to the spacially displaced outer end of coil 10. Individuals ordinarily skilled in the art of printed circuit board technology will recognize that coil 10, coil 10's geometry and the small effective diameter of each run within coil 10 is readily reproducible. Further, experimental tests have shown that a printed circuit board utilizing a run of copper having an effective diameter of 0.7 mils thereon, configured as illustrated in FIG. 1, is readily reproducible and coils constructed in accordance with this invention have relatively matching and comparable impedances within the desired operating range. The matched impedances of the coils are desirable when the coils are utilized in eddy current probes.

Figure 2:
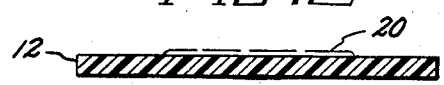
FIG. 2 illustrates a magnified side view, from the perspective of sectional line 2—2' in FIG. 1, of the excited eddy current coil.

FIG. 2 is a side view of the printed circuit board in FIG. 1 as viewed from the perspective of sectional line 2—2'. Insulative substrate 12 is illustrated as substantially planar with a substantially uniform electromagnetic field 20 extending normal from its surface when coil 10 is excited. Electric leads are coupled to solder pads 16 and 14 respectively by means well known in printed circuit board technology.

Figure 3:
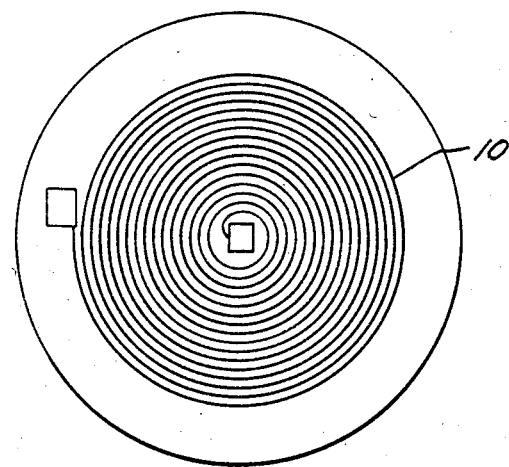
FIG. 3 illustrates a different geometric configuration of the eddy current coil.

FIG. 3 illustrates a different geometric configuration of coil 10 wherein the coil is a circular rather than rectangular spiral-like run of metal.

Figure 4:
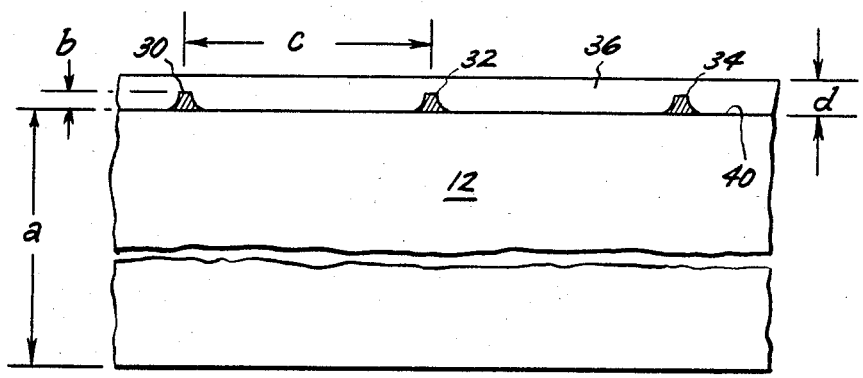
FIG. 4 illustrates a greatly magnified side view of the eddy current coil as viewed from the perspective of sectional line 4—4' of FIG. 1.

FIG. 4 is a magnified side view of three windings of coil 10 as viewed from the perspective of sectional line 4—4' in FIG. 1. Three distinct turns 30, 32, and 34 of the run of metal of coil 10 are illustrated in FIG. 4. To protect the coil from the ambient environment, a protective insulative layer 36 substantially covers the coil. Layer 36 is adapted to present only a minimal mechanical barrier between the coil and the region of semi-conducting or conducting material under the flaw detection test.

In the example under consideration herein, where a hair line surface crack is sought to be detected in the surface and sub-surface region of a block of carbon, and the sub-surface depth of penetration of the eddy current is limited to approximately 35 mils, the following dimensions for coil 10 and substrate 12 are utilized. The fiber glass insulative substrate 12 is approximately 62 mils along dimension "a" in FIG. 4. As stated earlier, the effective diameter of the run of copper is 0.7 mils as grossly illustrated as dimension "b". Each winding is spaced apart approximately 8 mils as shown as dimension "c" from the centerline of winding 30 to the centerline of winding 32. Dimension "d" is the depth of layer 36 and is approximately 1 mil.

Those of ordinary skill in the art will recognize that the effective diameter of the run of copper and the spacing between each winding of the eddy current coil is based upon such factors as the resistivity of the material under test, the desired depth of penetration for the eddy current, and the liftoff distance between the effective centers of the windings and the surface of the material under test. Calculations based upon these parameters will determine the appropriate effective diameter of each winding as well as the spacing between each winding. It is to be recognized that the depth of layer 36, or dimension "d", is based upon many factors such as the abrasive characteristics of the surface of material under test, the effective diameter of the run of metal, and the ambient environment in which the eddy current probe is operated. It is to be understood the dimensions and compositions described herein are illustrative and disclose one working embodiment of the invention.

Although substrate 12 is illustrated as having a relatively planar surface 40, that surface may be slightly curved or cambered. The critical limitation to the amount of camber of surface 40 is based upon a calculation of the uniformity of the electromagnetic field extending relatively normal the coil 10 mounted on surface 40. The term "cambered" as used herein refers to a surface which is slightly concave or convex rather than perfectly flat.

Although substrate 12 is discussed herein as being a substantially solid insulative body, the substrate may be deflexible. For example, the substrate may be composed of a mylar plastic or similar insulative material having a dimension a between 0.25 and 30 mils. A coil affixed to such a substrate would produce an eddy current coil which is relatively flexible and which could be placed on a suitable support. The substrate may also be a solid body of saffire.

Figure 5:
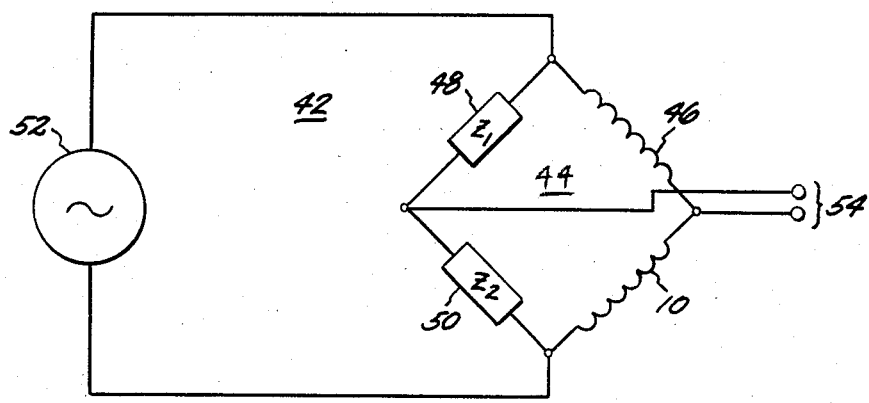
FIG. 5 is a schematic of a simple electrical circuit incorporating the eddy current coil.

FIG. 5 is a schematic of a simple electrical circuit including coil 10. Circuit 42 is part of the means for generating the electromagnetic field extending from coil 10. Circuit 42 includes a balanced impedance bridge circuit 44 which detects the impedance of coil 10. Coil 10 is one leg of bridge circuit 44 as is coil 46. Coil 46 is substantially similar to coil 10 but coil 46 is utilized as a reference for circuit 44. Adjustable impedance means 48 and 50 provide the two remaining legs of bridge circuit 44. Impedance means 48 and 50 are adjustable to balance bridge circuit 44 and an alternating current signal generator 52 provides power and an excitation signal to bridge circuit 44.

As is well recognized in the art of nondestructive testing, coil 10 is placed or juxtapositioned adjacent the region of material under test to induce an electromagnetic field in that region. The distance between the effective centers of the windings of the coil and the surface of material under test is generally recognized as the "liftoff" distance. As used herein, the term "region" refers to the combination of the surface area and sub-surface adjacent portions of the area of the referenced material. Coil 46 is substantially similar to coil 10 and the operation and establishment of a balanced bridge circuit 44 is well recognized in the art. Coil 46 is normally placed in relatively free space when coil 10 is so juxtaposed proximate an unflawed region of material, and impedance means 48 and 50 are adjusted such that bridge circuit 44 is either balanced or slightly unbalanced. An output signal at terminals 54 provides an indication of the integrity of the region of material under test, i.e., the output signal provides an indication whether the material is flawed or unflawed. Alternatively, coil 46 may be placed adjacent an unflawed region of material. When coil 10 is adjacent a region of material under test in such configuration, bridge circuit 44 generates a signal representative of the integrity of the region.

As is well recognized in the art, a reference signal must be established to determine whether the region of material under test is or is not flawed. One recognized procedure to establish this reference signal is to place coil 10 adjacent an unflawed region of material and balance circuit 44. A second recognized procedure is to establish a reference signal level based upon some theoretical calculations relating to coil 10, the frequency of excitation, and the material under test. Both of these procedures generate a reference signal corresponding to the impedance of coil 10 when the coil is adjacent an unflawed region of material under test. A third method, specifically related to the carbon block example, is to place coil 10 over an unflawed region substantially similar to the region of material to be tested for hair line cracks. In this fashion, the reference signal may reflect the influence of holes, copper pigtails or whatever in the subsurface region under test. A fourth method places coil 46 over an unflawed region and coil 10 over the region under test.

In one well known method of operation, bridge circuit 44 is adjusted to be slightly unbalanced when coil 10 is adjacent an unflawed region of material. As described herein, the term "slightly unbalanced" is synonymous with "substantially balanced". The output signal at terminals 54, when bridge circuit 44 is slightly unbalanced or substantially balanced, is a sinusoidal signal having a small amplitude. Thereafter, coil 10 is placed adjacent the region of material under test to induce an eddy current in the surface and sub-surface region of that material. If the region is unflawed, or the integrity of the material is maintained, the small amplitude sinusoidal output signal will be substantially unchanged. However, if the region of material is flawed, due to a crack in the material, an unexpected change in the composition of the material, or an unexpectedly thin layer of material (as contrasted with a thick layer) over a known base material, the output signal from bridge circuit 44 will reflect a substantially different sinusoidal output signal at terminals 54. In this manner, the output signal at terminals 54 supplied to a well known comparison means provides an indication of the integrity of the material under test by relating the reference signal to the output signal which is a signal representative of the impedance of coil 10 when the coil is adjacent the region of material under test.

Figure 6:
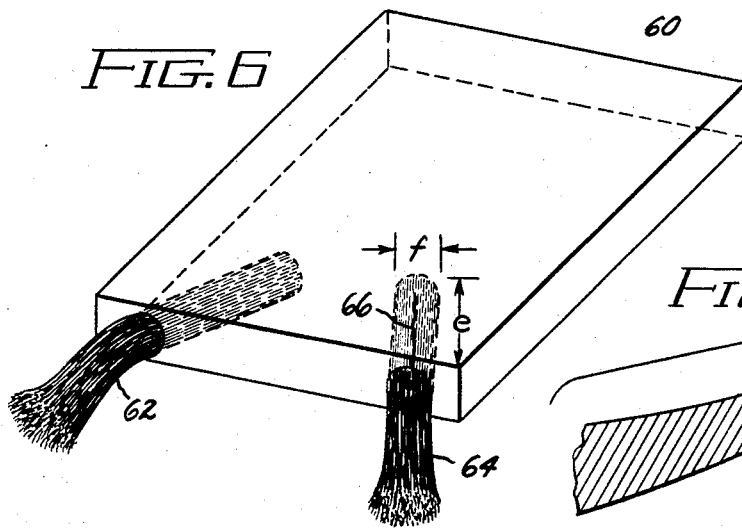
FIG. 6 illustrates one exemplary use of the invention herein.

FIG. 6 illustrates one type of material subject to testing by the eddy current probe described herein. Block 60 consists essentially of carbon. A pair of holes are drilled diagonally into block 60 and copper pigtails 62 and 64 are mechanically tamped into the two holes as illustrated in FIG. 6. In this example, block 60 has a thickness of approximately 205 mils and the diameter of each hole is approximately 128 mils. One particular use of block 60 is as a carbon brush, the carbon typically in the form of graphite, in certain dynamoelectric machines. The copper pigtails provide an electrical connection between carbon block 60 and the associated circuitry of the dynamoelectric machine. Nondestructively testing the surface area and sub-surface region immediately adjacent the copper pigtails determines whether a hair line crack has developed during the mechanical insertion of the pigtails 62 and 64 into block 60. A crack 66 is present due to pigtail 64's insertion. The surface area under test in this example is $\frac{1}{2}"$ by $\frac{1}{2}"$ as illustrated as dimensions "e" and "f" respectively in FIG. 6. Due to surface area "e"×"f", a somewhat rectangular but spiral-like eddy current coil illustrated in FIG. 1 is utilized.

Hair line crack 66 affects the eddy currents induced in the surface and sub-surface region of block 60 when coil 10 is juxtaposed to area "e"×"f" thereby altering the output signal at terminals 54 of the bridge circuit 44. An electronic circuit, associated with circuit 42, amplifies and filters the output signal to determine the presence of crack 66.

Since the holes for receiving pigtails 62 and 64 are respectively centered on the edge of block 60 as shown in FIG. 6, there are minimally approximately 38.5 mils of block 60 between copper pigtails 62 and 64 when inserted into cooperating holes and the upper surface of block 60. It is desired to determine the integrity of block 60 after inserting pigtails 62 and 64. In order to avoid interference with and/or distortion of measurements by the conductive copper of pigtail 64 when attempting to detect crack 66 above pigtail 64, it is necessary to limit the depth of penetration of eddy currents induced in block 60, for example to a depth of 35 mils, to inhibit induction of eddy currents in pigtail 64. A similar depth limitation is required when the surface and sub-surface region above pigtail 62 is to be examined.

Figure 7:
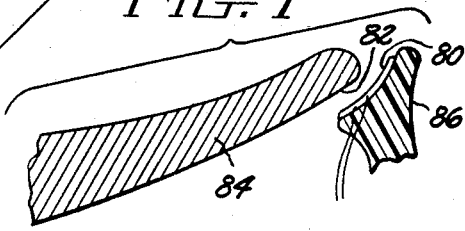
FIG. 7 illustrates another utilization of the present invention with a substantially planar but cambered unilaminar coil.

FIG. 7 illustrates another utilization of the eddy current coil herein. Coil 80 is substantially planar but cambered to match cambered surface 82 of structure 84. As illustrated, the coil is slightly concave to geometrically approximate the slightly convex surface 82. Coil 80 is supported by insulative support structure 86 which is similarly cambered. As is well recognized in the art, to obtain accurate nondestructive testing results, the liftoff distance between the effective centers of the windings of the eddy current coil and the surface of the material under test must be maintained at a relatively constant and acceptable level. An eddy current coil constructed with a flexible insulative substrate, as described herein, could be placed on a slightly cambered support structure, such as structure 86, to maintain that liftoff distance between the contoured surface 82 of a structure 84 under test. Accordingly, the contour of support 86 could be altered to match the contour of surface 82 thereby maintaining an acceptable lift-off distance.

As is well recognized in the art, eddy current probes can be utilized to determine cracks in materials, inclusions in materials, to determine the thickness of a particular conductive or semi-conductive material disposed as a layer on a base material, and to generally determine the structural and metallurgical integrity of a host of materials. The invention herein is not intended to be limited by the specific uses described herein. Also, it is recognized by those of ordinary skill in the art that many electronic circuits are capable of detecting the impedance of an eddy current coil, generating a reference signal, and comparing the reference signal to the impedance of the coil when the coil is adjacent a region of material under test. The simple electronic circuit described herein, in association with the eddy current coil, is not meant to limit the scope of this invention. The claims appended to this specification are meant to encompass the modifications described herein and those modifications apparent to individuals of ordinary skill in the art.

We claim:

1. A method for detecting a flaw in a surface and/or sub-surface region of a semi-conductive material, the semi-conductive material including a conducting material disposed in the sub-surface region at a predetermined distance from the surface of the semi-conductive material, comprising the steps of:

providing a continuous run of metal configured spiral-like on a substantially planar insulative substrate as a unilaminar coil;

exciting said coil to produce an electromagnetic field extending from said coil, the electromagnetic field for inducing eddy currents in the surface and/or sub-surface region of the semi-conductive material when said coil is positioned adjacent said semi-conductive material;

establishing a reference signal corresponding to the impedance of said coil when said coil is adjacent an unflawed region of said material;

juxtapositioning said coil adjacent the surface and/or sub-surface region of the semi-conductive material to induce an electromagnetic field therein, while inhibiting induction of eddy currents in the conducting material; and comparing a signal representative of the impedance of said coil during said juxtapositioning step with said reference signal to provide an output signal indicative of the integrity of said surface and/or sub-surface region of the semi-conductive material, whereby the flaw in the surface and/or sub-surface region of the semi-conductive material may be detected.

2. A method for detecting a flaw in a surface and/or sub-surface region of a semi-conductive material, the semi-conductive material including a conducting material disposed in the sub-surface region at a predetermined distance from the surface of the semi-conductive material, comprising the steps of:

providing a continuous run of metal configured spiral-like on a substantially planar but cambered flexible insulative substrate as a uilaminar coil;

exciting said coil to produce an electromagnetic field extending from said coil, the electromagnetic field for inducing eddy currents in the surface and/or sub-surface region of the semi-conductive material when said coil is positioned adjacent said material;

establishing a reference signal corresponding to the impedance of said coil when said coil is adjacent an unflawed region of said material;

juxtapositioning said coil adjacent the surface and/or sub-surface region of the semi-conductive material to induce an electromagnetic field therein, while inhibiting induction of eddy currents in the conducting material; and comparing a signal representative of the impedance of said coil during said juxtapositioning step with said reference signal to provide an output signal indicative of the integrity of said surface and/or sub-surface region of the semi-conductive material, whereby the flaw in the surface and/or sub-surface region of the semi-conductive material may be detected.

3. The method as in claim 1 or 2, wherein said metal is substantially copper and said coil and said substrate is a printed circuit board.

4. The method as in claim 1 or 2, wherein exciting includes coupling an excitation signal at a frequency equal to or greater than 7 megahertz to said coil.

5. The method as in claim 4, wherein the step of establishing a reference signal includes using a substantially balanced impedance bridge circuit having the coil as one of its legs.

6. The method as in claim 1 or 2, wherein said semi-conductive material consists essentially of carbon and said flaw to be detected is a harline crack in said surface and/or sub-surface region of said semi-conductive material, and further wherein a copper pigtail is disposed in said semi-conductive material at the predetermined distance from the surface of the semi-conductive material.

7. The method as in claim 6, wherein the step of inhibiting includes exciting said coil at a frequency high enough to inhibit induction of eddy currents in the copper pigtail.

8. The method as in claim 6, wherein the carbon is in the form of graphite.

* * * * *